(12) United States Patent
Soman et al.

(10) Patent No.: US 8,110,229 B2
(45) Date of Patent: Feb. 7, 2012

(54) HERBAL COMPOSITION FOR REDUCING ADD/ADHD AND METHOD THEREOF

(75) Inventors: Girish Sudhakar Soman, Maharashtra (IN); Shrikrishna Govind Phadke, Maharashtra (IN)

(73) Assignee: Nisarga Biotech Pvt Ltd., Maharashtra (IN)

( * ) Notice: Subject to any disclaimer, the term of this patent is extended or adjusted under 35 U.S.C. 154(b) by 100 days.

(21) Appl. No.: 12/663,406

(22) PCT Filed: Apr. 17, 2009

(86) PCT No.: PCT/IN2009/000239
§ 371 (c)(1),
(2), (4) Date: Dec. 7, 2009

(87) PCT Pub. No.: WO2009/136410
PCT Pub. Date: Nov. 12, 2009

(65) Prior Publication Data
US 2010/0166893 A1    Jul. 1, 2010

(30) Foreign Application Priority Data
Apr. 19, 2008  (IN) .......................... 2079/MUM/2007

(51) Int. Cl.
*A61K 36/00* (2006.01)
*A61K 36/53* (2006.01)
*A61K 36/55* (2006.01)
*A61K 31/355* (2006.01)
*A61K 36/906* (2006.01)

(52) U.S. Cl. ........ 424/725; 424/756; 424/768; 424/745; 514/458

(58) Field of Classification Search .................. None
See application file for complete search history.

(56) References Cited

U.S. PATENT DOCUMENTS

| 5,719,178 A | 2/1998 | Paul et al. |
| 6,093,404 A | 7/2000 | Kattan |
| 6,541,043 B2 | 4/2003 | Lang |
| 6,759,053 B2 | 7/2004 | DiSanto |
| 2004/0152737 A1 | 8/2004 | Hertel et al. |
| 2005/0142232 A1 * | 6/2005 | Pushpangadan et al. ..... 424/764 |

FOREIGN PATENT DOCUMENTS

| DE | 2740041 A | * | 3/1979 |
| NZ | 530554 A | * | 4/2004 |
| WO | 03068251 A1 | | 8/2003 |

OTHER PUBLICATIONS

Xi et al, Effects of supplementary linseed oil on learning and memory ability of filial generation mice, Zhongguo Yaowu Yu linchuang (2006), 6 (10), 733-735.*

Natural COX-2 Inhibitor for Joint Comfort (Source Naturals) 2003 (2003) http://www.sourcenaturals,com/products/print/GP1724/ and http://vitanetonline.com/description/SN1579/vitamins/Inflama-Rest/ (viewed Aug. 17, 2011).

Bhattacharya et al., Effect of Mentat, a Herbal Formulation, on Experimental Models of Alzheimer's Disease and Central Cholinergic Markers in Rats, Fitoterapia (1995). (LXVI), 3, 216].

The Disease of Preventive Power of Fish and Olives (Life Extension) http://www.lef.org/magazine/mag2005/dec2005_supp_mediterranean_01.htm (viewed Aug. 17, 2011).

Peng et al., Supercritical Fluid Extracts of Rosemary Leaves Exhibit Potent-Anti-Inflammation and Anti-Tumor Effects. Sep. 7, 2007. Biosci. Biotechnol. Biochem. (71) 9 p. 2223-2232.

International Search Report dated Nov. 17, 2009 issued to PCT/IN2009/00239.

* cited by examiner

*Primary Examiner* — Qiuwen Mi
(74) *Attorney, Agent, or Firm* — Kramer & Amado, P.C.

(57) ABSTRACT

Disclosed herein is a herbal composition comprising supercritical fluid extracts/oils of Jyotishmati, *Bacopa monnieri*, Ginger Oil, Flax Seed oil, Rosemary Ext and Vitamin E in an effective amounts useful in the treatment of symptoms associated with Attention Deficit disorder (ADD) and Attention deficit/hyperactivity disorder (ADHD).

14 Claims, 4 Drawing Sheets

Figure 1:
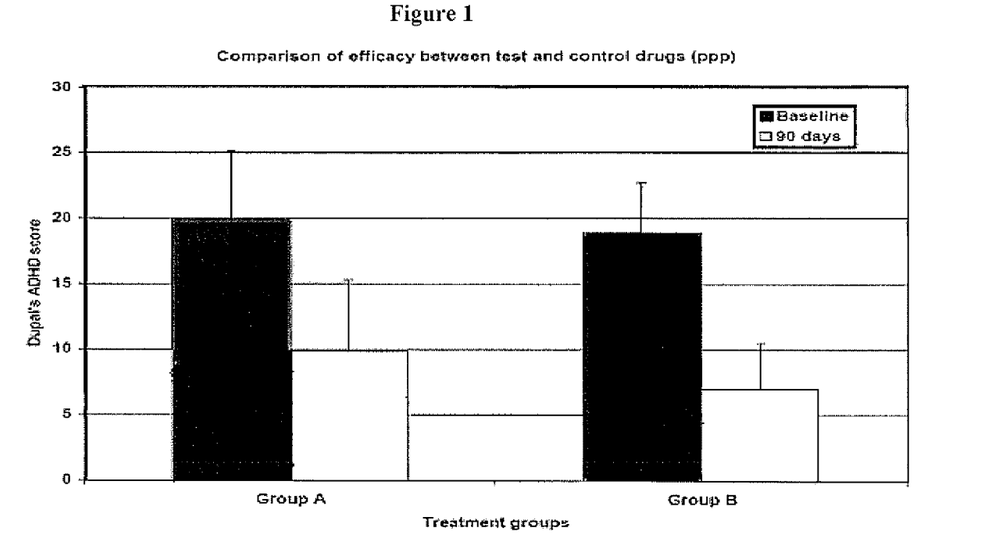
FIG. 1 shows Comparison of efficacy between Capsule C and placebo in 90 days.
Figure 2:
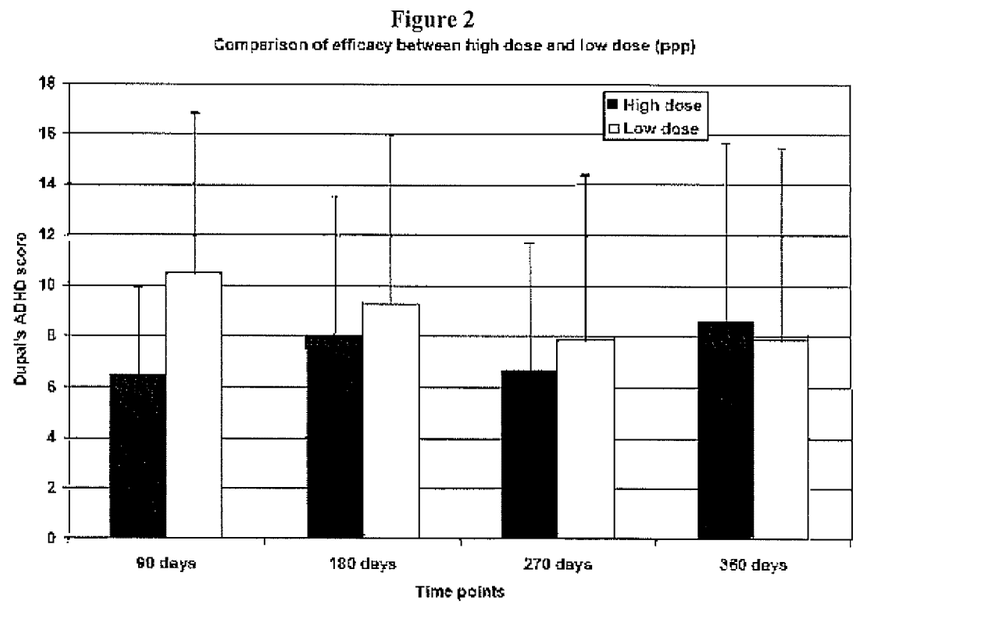
FIG. 2 shows Comparison of efficacy between two doses of Capsule C over a long term application for duration of 275 to 365 days.
Figure 3:
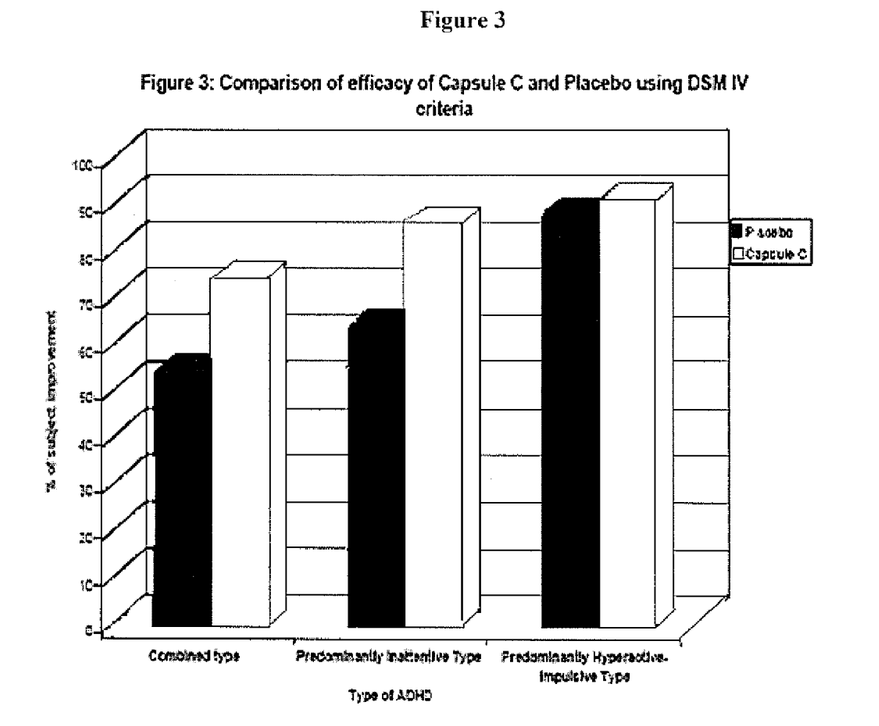
FIG. 3 shows Comparison of efficacy between Capsule C and placebo using DSM IV criteria
Figure 4:
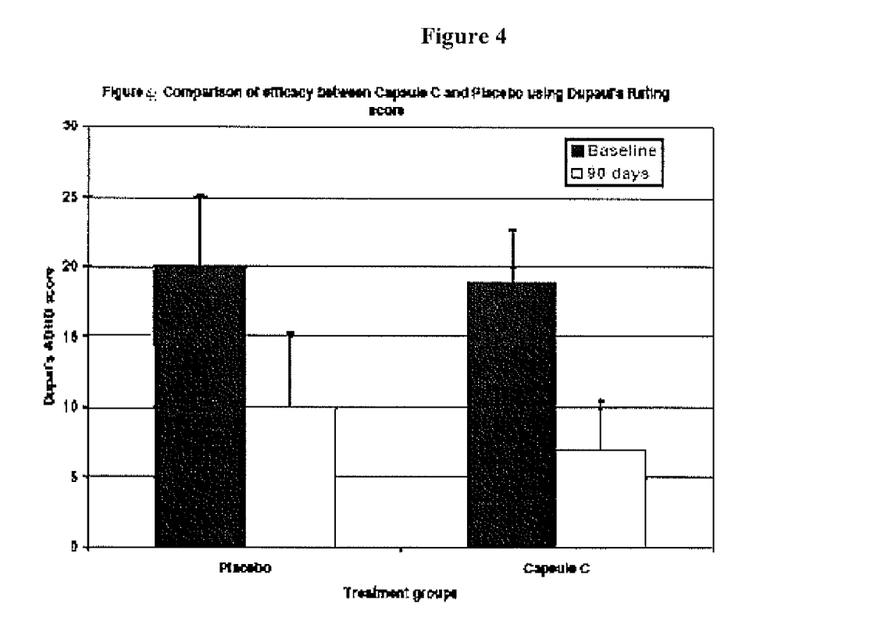
FIG. 4 shows Comparison of efficacy between Capsule C and placebo using Dupaul's Rating score
Figure 5:
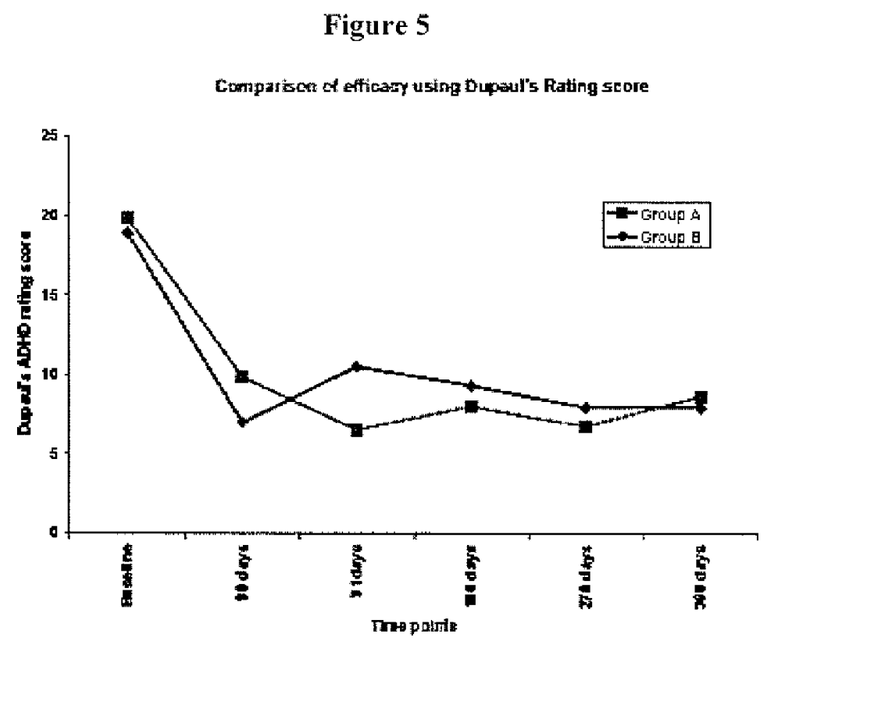
FIG. 5 shows Comparison of efficacy between Group A and Group B using Dupaul's Rating score
Figure 6:
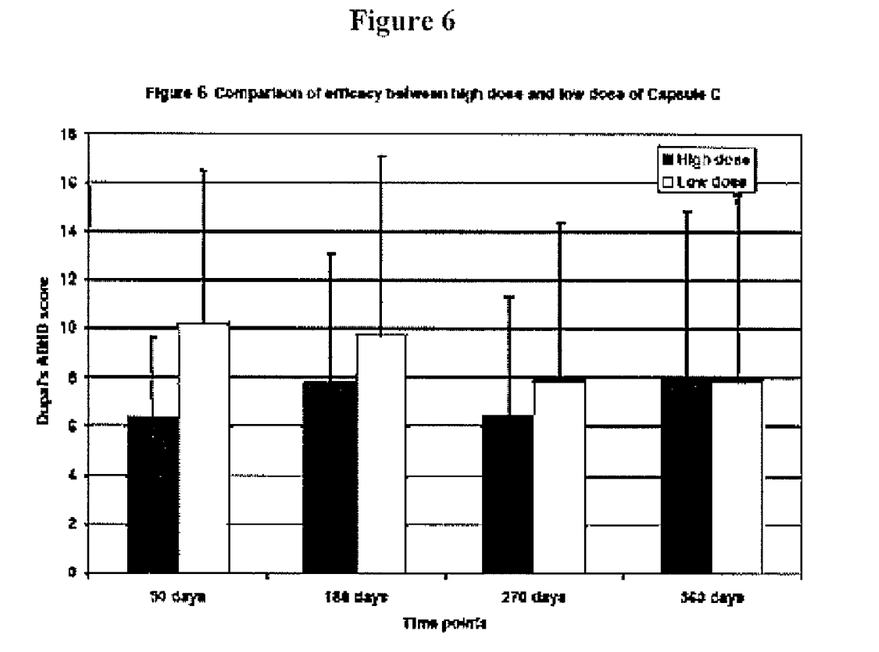
FIG. 6 shows Comparison of efficacy between high dose and low dose of Capsule C
Figure 7:
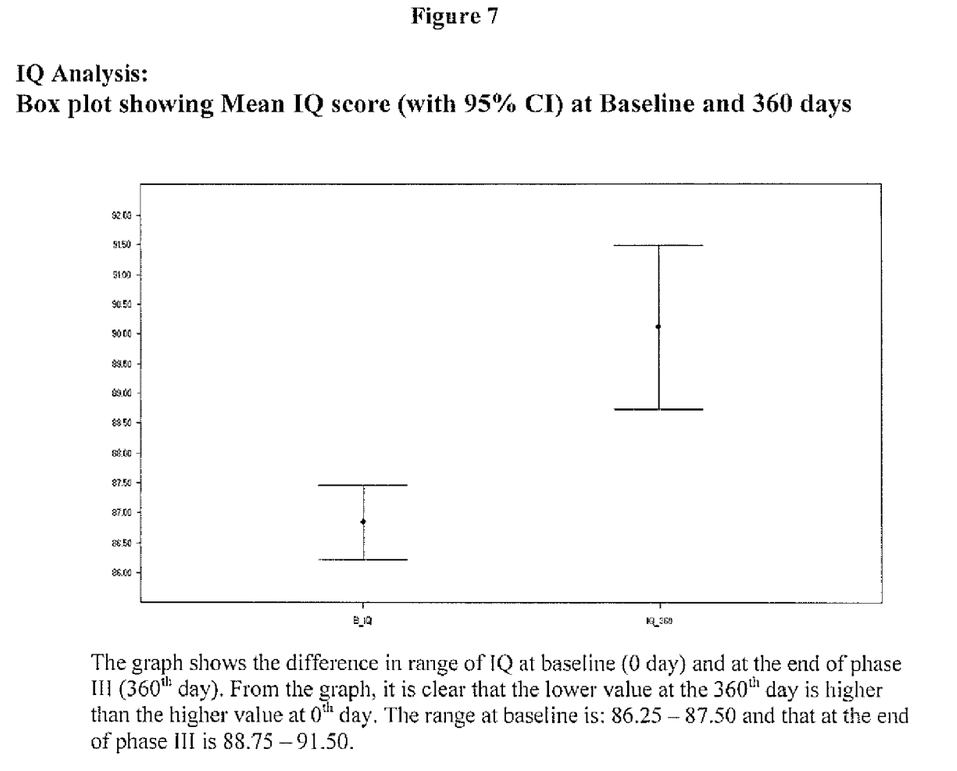
FIG. 7 shows box plot showing Mean IQ score (with 95% CI) at Baseline and 360 days

IQ Analysis:
Box plot showing Mean IQ score (with 95% CI) at Baseline and 360 days The graph shows the difference in range of IQ at baseline (0 day) and at the end of phase III (360th day). From the graph, it is clear that the lower value at the 360th day is higher than the higher value at 0th day. The range at baseline is: 86.25 – 87.50 and that at the end of phase III is 88.75 – 91.50.

Figure 8

Figure 8:
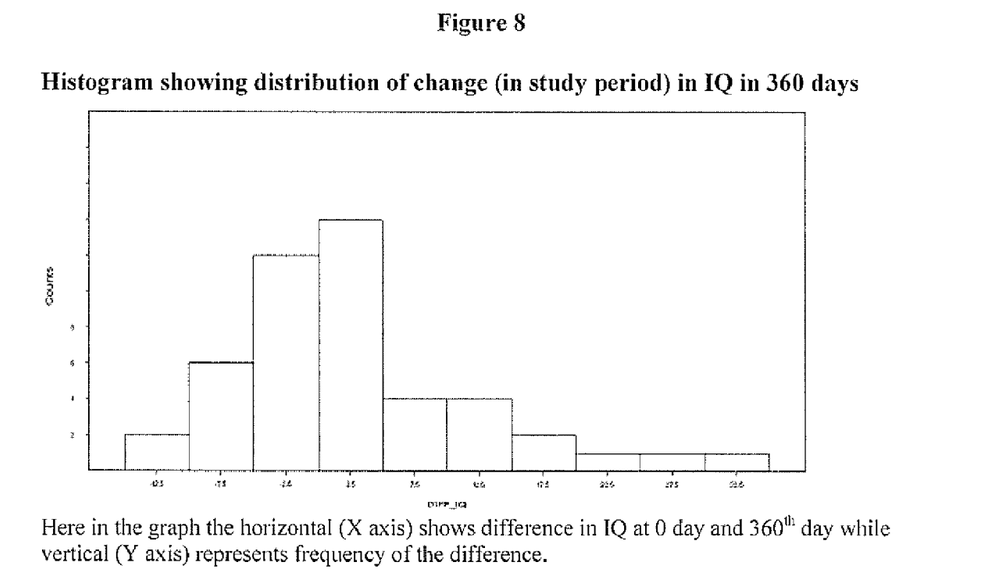
FIG. 8 shows histogram showing distribution of change (in study period) in IQ in 360 days

Histogram showing distribution of change (in study period) in IQ in 360 days

Here in the graph the horizontal (X axis) shows difference in IQ at 0 day and 360th day while vertical (Y axis) represents frequency of the difference.

HERBAL COMPOSITION FOR REDUCING ADD/ADHD AND METHOD THEREOF

TECHNICAL FIELD

The present invention relates to synergistic herbal compositions useful in the treatment of Attention Deficit disorder (ADD) and Attention deficit hyperactivity disorder (ADHD). More particularly the invention relates to a herbal composition capable of reducing the ADD/ADHD symptoms, which also helps to improve memory and cognitive skills in adolescents and adults. The invention further relates to method for treating the same.

BACKGROUND AND PRIOR ART

Attention Deficit Disorder (ADD) and Attention Deficit Hyperactivity Disorder (ADHD) (severally and collectively hereinafter referred to as "ADHD") are developmental disorders, largely neurological disorders affecting 5% of the world population. The disorder typically presents itself during childhood, and is characterized by a persistent pattern of inattention and/or hyperactivity, as well as forgetfulness, poor impulse control or impulsivity, and distractibility.

Inattentive behaviour is often characterized by difficulty focusing on one task, failure to pay attention to details, and making careless mistakes in a variety of tasks. Individuals exhibiting inattentive behavior may appear as if their minds are elsewhere or they are not listening or did not hear what has just been said.

Hyperactive people always seem to be in motion and may suffer from feelings of restlessness and difficulty engaging in sedentary activities. Common signs include excessive unproductive movement, excessive talking, and an inability to sit still. Hyperactive children often roam around the room, and feel compelled to touch everything.

Impatience and a failure to think before acting often characterize impulsivity. Impulsive young children may frequently interrupt others, fail to listen to directions, and have difficulty waiting for their turn.

These problems are reflected in impairment of a person's will or capacity to control his or her own behavior relative to the passage of time and to keep future goals and consequences in mind. ADHD is most commonly diagnosed in children and, over the past decade, has been increasingly diagnosed in adults. About 60% of children diagnosed with ADHD retain the disorder as adults.

Studies indicate that the disorder is highly heritable and that genetics contribute about three quarters of the total ADHD population. While the majority of ADHD is believed to be genetic in nature, ⅕ of all ADHD cases are thought to be acquired after conception due to brain injury caused by either toxins or physical trauma parentally or postnatally. Scientists have not yet identified a single underlying cause behind these behavior characteristics. While some have been linked to decreased brain activity, the biological reason for the decreased brain activity is still unknown. Treatment for ADD and ADHD is therefore limited to treating the symptoms of the disorders.

Methods of treatment usually involve some combination of medications, behaviour modifications, life style changes, and counseling.

The most common treatment for ADD and ADHD is the use of mild central nervous system stimulant drugs, such as Ritalin, Cylert, and Dexedrine. However, there are several drawbacks in using these drugs such as frequent short-term side effects include insomnia, loss of appetite, headaches, stomachaches, hyperactivity, drowsiness, blood pressure and pulse changes, and cardiac arrhythmia. In addition to this, the possible consequences of long-term exposure to these drugs in children are not thoroughly investigated. The use of Ritalin in children under six years of age is particularly undesirable since safety and efficacy in this age group has not been established.

As an alternative to the aforementioned conventional treatments, U.S. Pat. No. 5,719,178 discloses a method for treating ADHD comprising taking a quantity of proanthocyanidin sufficient to relieve symptoms of ADHD every 3.5 to 4.0 hours. A heterocyclic antidepressant, preferably desipramine may be taken optionally with the proanthocyanidin in quantities sufficient to attenuate ADHD-related symptoms of lack of cognitive focus. However, a major drawback of this method is that repeated doses are required to alleviate symptoms throughout the day, which is inconvenient as well as difficult especially for school going children.

U.S. Pat. No. 6,093,404 describes a therapeutic composition for treatment of ADD or ADHD comprising in percentage by weight: 3-9% proanthocyanidin, 30-40% yucca root, 15-25% hawthorn berry, 10-20% bilberry, 5-15% silymarin, and 10-15% gingko biloba.

U.S. Pat. No. 6,759,053 provides compositions and methods for using the S(+) enantiomer of desmethylselegiline (N-methyl-N-(prop-2-ynyl)-2-am-inophenylpropane), for the treatment of selegiline-responsive diseases and conditions. Diseases and conditions responsive to selegiline include those produced by neuronal degeneration or neuronal trauma and those due to immune system dysfunction. Effective dosages are a daily dose of at least about 0.015 mg/kg of body weight.

The use of 3-[1-[2-(1-acetyl-2,3-dihydro-1H-indol-3-yl)ethyl]-1,2,3,6-tetr-ahydropyridin-4-yl]-6-chloro-1H-indole, any of its enantiomers and pharmaceutically acceptable salts thereof for the preparation of a pharmaceutical composition for the treatment of Attention Deficit Hyperactivity disorder is disclosed in US20040152737.

The pharmaceutical compositions are comprised of a therapeutically effective combination of a nicotine receptor partial agonist and an anti-ADHD agent and a pharmaceutically acceptable carrier and the method of using these compounds is disclosed in US20040220184

WO2003068251 describes herbal formulation comprising *Bacopa monneri; Centella asiatica; Glcyrrhiza glabra; Withania somnifera* and *Celastrus paniculatus* and process for preparing the same for treating Attention Deficiency Disorder in Humans. The herbs are subjected to solvent extraction using hazardous solvents such as hexane, chloroform, methanol and acetone. The herbs are extracted especially Brahmi and Jyotishmati using Hydrocarbon solvents such as Hexane, Chloroform which are considered hazardous to human health. The extraction of the herbs at higher temperature destroys or modifies molecular and chemical structure of temperature sensitive phytochemicals which may contribute to the therapeutic value of the herbs.

In a conventional solvent extraction process, the separation temperature is always greater than the extraction temperature. This means that when the solvent is recovered, the obtained extract is subjected to higher temperature, which is likely to destroy many temperature sensitive phyto nutrients and phyto chemicals in the extract.

A combination of hyperforin, 5-hydroxy triptophan, rhodiola rosea, along with Vitamins B, Vitamin C, Vitamin D3, and minerals like selenium and Zinc are sold under the brand name of Amoryn for treating ADHD disorders. The daily dose comprises 1 to 4 capsules per day.

There is a need in the art to provide herbal formulation for oral administration comprising safe and effective extracts of two or more herbs, effective for the treatment of ADHD, and is devoid of any side effects.

SUMMARY OF THE INVENTION

Accordingly, in one aspect, the invention discloses herbal composition comprising two or more effective extracts of the herbs selected from *Acorus calamus, Azadirchta indica, Bacopa monnieri, Boswellia serrata, Eclipta alba, Embelia ribes, Fumaria indica, Linum usitatissimum, Celastrus paniculatus, Mucuna pruriens, Nardostachys jatamansi, Nigella sativa, Ocimum sanctum, Phyllanthus niruri, Rosmarinus officinalis, Ricinus communis, Valeriana officianalis* and *Zingiber officinale* useful in the treatment of ADHD.

In another aspect, the invention discloses method of extraction of the herbs used in the invention. The herbs are extracted using a unique method of extraction, so as to ensure that the extractives are safe and effective and contains no harmful extraction solvents.

The supercritical CO2 extraction which is used in the present invention with or without entrained ethanol does not leave any hazardous solvent residues. The extraction temperature is maintained between 35° C. to 45° C., which ensures the retention of all temperature sensitive ingredients.

The method adopted by the present inventors for extraction (Supercritical CO2 extraction with or without entrained ethanol) always has a much lower separation temperature than the extraction temperature. Thus integrity of phytonutrients and phytochemicals is maintained apart from retaining the temperature sensitive ingredients (Typical separation temperature for conventional extraction is 45° to 80° C. while the separation temperature will be around 20° C. to 25° C. in the present process) So in conventional extraction separation temperature for recovering the solvent from extracted material is always higher than the extraction temperature.

In a further aspect, the invention describes a method of treating Attention Deficit Disorder (ADD) and Attention Deficit/Hyperactivity Disorder (ADHD) using the compositions of the present invention. The invention also relates to using the formulation/composition for improving cognitive skills and memory.

DETAILED DESCRIPTION

In accordance with the above aspects, the invention will now be described in detail in connection with certain preferred and optional embodiments, so that various aspects thereof may be more fully understood and appreciated.

As described herein 'Capsule C' means and includes a capsule containing 100 mg of the herbal ingredients of the invention.

The phrase 'composition of the invention' herein mentioned below encompasses all the herbal formulations/compositions/dosage forms disclosed in the invention.

The phrase 'higher dose' herein mentioned below encompasses dosage of 300 mg of the composition two times a day (3 capsules of 100 mg two times a day or 1 capsule of 300 mg two times a day)

The phrase 'lower dose' herein mentioned below encompasses dosage of 200 mg of the composition two times a day (2 capsules of 100 mg two times a day OR 1 capsule of 300 mg containing 200 mg of composition and 100 mg of sesame oil, two times a day)

The present invention describes herbal compositions for oral application comprising mixture of extractives of two or more herbs selected from *Acorus calamus, Azadirchta indica, Bacopa monnieri, Boswellia serrata, Eclipta alba, Embelia ribes, Fumaria indica, Linum usitatissimum, Celastrus paniculatus, Mucuna pruriens, Nardostachys jatamansi, Nigella sativa, Ocimum sanctum, Phyllanthus niruri, Rosmarinus officinalis, Ricinus communis, Valeriana officianalis* and *Zingiber officinale* useful in the treatment of ADHD and improving memory and cognitive skills.

The herbs are extracted using a unique method of extraction, so as to ensure that the extractives are broad spectrum (meaning with more number of phytoconstituents), safe and effective and contains no harmful extraction solvents such as Hexane, Acetone and Chloroform.

The principal characteristics of ADHD are inattention, hyperactivity and impulsivity. Some of the disorders known to be accompanying ADHD are learning disabilities (LD), Tourette syndromes, and oppositional defiant disorder; conduct disorder, anxiety and depression or Bipolar disorder.

There are many herbs reported in Ayurveda and other alternative medicines known to work on brain functions. Therefore, the inventors of the present invention have undertaken screening strategy of many plant extracts using in vitro cell based experimental protocols followed by in vivo experimental studies and found that the extracts of the following plants are known to work on brain functions.

Accordingly, the current invention uses a mixture of extractives of two or more herbs selected from *Acorus calamus, Azadirchta indica, Bacopa monnieri, Boswellia serrata, Eclipta alba, Embelia ribes, Fumaria indica, Linum usitatissimum, Celastrus paniculatus Mucuna pruriens, Nardostachys jatamansi, Nigella sativa, Ocimum sanctum, Phyllanthus niruri, Rosmarinus officinalis, Ricinus communis, Valeriana officianal* and *Zingiber officinale.*

The details of the herbs used in the present invention are as mentioned below:

Celastrus Paniculatus:

*Celastrus Paniculatus* is known as Jyotishmati, consists of dried, brownish-orange, ripe seeds, devoid of capsule wall of *Celastrus Paniculatus* wild. It is a large climbing shrub with yellow to brownish orange fruits. Mostly found all over the hilly parts of the country up to an altitude of 1200 m.

Parts used for the purpose of the present invention are fruits including Seeds. Oil derived from these fruits seeds is used for therapeutic application for this invention.

Analysis of Fatty Acids of Jyotishmati (*Celastrus Paniculatus*) Oil Using Gas Chromatography:

Weighed quantity of sample Jyotishmati (*Celastrus Paniculatus*) oil was dissolved in methanol and few drops of Sulphuric acid added to it. The mixture was refluxed on water bath for 3 hours; allow cooling and extracting with petroleum ether with the addition of water. Discarded the aqueous layer, wash the petroleum ether layer with water 4-5 times, till the washings are neutral. Evaporate the petroleum ether and weighed the residue. Dissolve the residue in acetone and injected into GC system.

Constituents like palmitic acid, stearic acid. Oleic acid, Linolenic acid and Linoleic acids are identified by G.C.

*Linum usitatissimum:*

*Linum usitatissimum* is known as Flax Seed, belongs to Family called Linaceae having synonyms like Linseed, Atshi, Uma, Atasi. Atasi consists of dried, ripe seeds of *Linum usitatissimum* Linn, an erect annual herb, 0.6-1.2 m high.

This plant is extensively cultivated throughout the plains of India up to an altitude of 800 m, capsule ripens by end of June, dried seeds separated from capsule by thrashing.

Dried Seeds of the plant is used for the purpose of the present invention. Oil extracted using these seeds is used for the preparation of formulation.

Analysis of Fatty Acids of the Flax Seed Oil Using Gas Chromatography:

Weighed quantity of sample was dissolved in methanol and few drops of Sulphuric acid added to it. The mixture was refluxed on water bath for 3 hours, allowed to cool and extracted with petroleum ether with the addition of water. Discarded the aqueous layer, washed the petroleum ether layer with water 4-5 times, till the washings are neutral. Evaporated the petroleum ether and weighed the residue. Dissolved the residue in acetone and injected into GC system.

Constituents like palmitic acid, stearic acid. Oleic acid, Linolenic acid and Linoleic acids are identified by G.C. using appropriate column.

*Bacopa monnieri:*

*Bacopa monnieri* belongs to family called Scrophulariaceae:

This plant is distributed throughout India in wet and damp places ascending to an altitude of 1320 m. The whole Plant is used for the purpose of present invention. CO2 extract derived from the whole plant is used for therapeutic application for this invention.

Ginger Extract:

Ginger Extract is taken from the plant called *Zingiber officinale* which belongs to Family Zingiberaceae. This plant is universally known and widely cultivated all over the warm, moist parts of India. It is a perennial herb with a stout, horizontal, tuberous, jointed, rootstock. The rhizome is thick and fleshy, laterally compressed bearing short, ovate, oblique branches on the upper surface. CO2 extract from the dried rhizomes of the plant is used for the purpose of present invention.

Rosemary Extract:

Rosemary Extract is taken from the plant called *Rosmarinus officinalis* which belongs to a family called Labiatae. This plant is a native of Mediterranean regions & covers a wide range in southern Europe & now it is cultivated throughout the world. Plant consists of dried leaves, stems. Herb of Rosemary has several ash coloured branches & bark is rather scaly & grows up to height of 3 feet. CO2 extract from the Aerial parts of this plant are used in the present invention.

In a preferred embodiment, all the herbal extracts used in the formulation are extracted using Supercritical CO2 extraction with or without entrained solvent ethanol, using the below mentioned conditions.

Pressure of extraction: Between 72 kg/cm$^2$ to 550 kg/cm$^2$
Preferred Range: 300 kg/cm$^2$ to 400 kg/cm$^2$
Entrained ethanol 0-10% (Preferred range 3 to 7%)

All the extracts used are free from any hydrocarbon solvent residues such as Hexane, chloroform, Acetone etc, which are hazardous to human health when ingested even at very low residual levels.

The herbs can also be extracted using any conventional methods such as cold pressing method, conventional extruder press method, solvent extraction, distillation "Modified Atmosphere Packing" (MAP).

Supercritical CO2 extraction is a process that produces a broad spectrum of the herbs lipophilic constituents such as oils, fatty acids along with vital temperature sensitive phytonutrients. The spectrum of the extractives can be widened by using up to 10% of ethanol as an entrained solvent along with pure $CO_2$. The major advantages of using this process of extraction are retention of all the temperature sensitive ingredients present in the herb which contributes toward health benefits. Unlike other solvent extraction methods such as Hexane, Chloroform, Acetone, the resulting extract is free of hazardous solvent residues. Similarly, the resultant extract is also free from heavy metals contamination as heavy metals are not soluble in $CO_2$ or alcohol.

The phrase 'composition of the invention' herein mentioned below encompasses all the herbal formulations/compositions/dosage forms disclosed in the invention.

In a preferred embodiment, the composition of the present invention comprises: Jyotishmati oil (*Celastrus paniculatus* seed oil) in an amount of about 5 to 50% of the total formulation; Flax seed oil (*Linum usitatissimum* seeds) in an amount of about 30 to 65%; *Bacopa monnieri* extract in an amount of about 0 to 10%; *Rosmarinus officinalis* extract 0-10%, Ginger extract in an amount of 0 to 4% and natural Vitamin E ($\alpha$ Tocopherols) in an amount of 0 to 2%.

The present formulations are optionally formulated using suitable pharmaceutical excipients such as diluents, binders, lubricants, disintegrants, pharmaceutical oils, herbal carrier oils such as Sesame oil, Palm oil etc; and bases and the like known to a skilled person in the art.

Major Chemical Constituents in Individual Ingredients are as Below:

The Major Chemical Constituent of Jyotishmati Oil $CO_2$ is Linoleic acid (Omega 6)-(Area % by GC): 9.00% to 12.00%

The Major Chemical Constituent of Flax seed Oil $CO_2$ is Linolenic acid (Omega 3)-(Area % by GC): 50.00% to 60.00%

The Chemical Constituents of *Bacopa* Extract CO2 is Bacosides: 20.00 to 30.00%

The Chemical Constituents of Ginger Extract CO2 is Gingerols in an amount of greater than 10.00% and *Zingiberene* in an amount of greater than 10.00%.

The major chemical constituent in Rosemary Extract CO2 is B-Sitosterols in an amount ranging 8.00%-13.00%.

All the five ingredients from (1) to (5) are extracted with Supercritical CO2 extraction with or without entrained solvent ethanol.

The amount of the herbal extracts/oils used in the 'composition of the invention' is preferably as follows:

Jyotishmati oil CO2 in lower dose ranges from 20-26%, while in higher dose 32-38%.

Similarly, *Bacopa monnieri* extract CO2 in lower dose ranges 2-6% whereas in higher dose it ranges from 4-7%.

The presence of Ginger oil (T) CO2 varies from 0.5-0.8% in lower dose however, 0.5 to 1.5% in higher dose.

The Flax seed oil CO2 used in lower dose is 32-40% where as in higher dose is 51-58%.

Rosemary extract CO2 is used in the range of 2-5% in lower dose and 3.0 to 6.0% in higher dose.

Similarly vitamin E is used in 0.17% to 0.30% in lower dose and 0.3 to 0.6% in higher dose.

Sesame oil used in lower dose is 30-35% where as the higher dose does not contain sesame oil.

Alternatively 200 mg lower dosage twice a day without sesame oil can be administered:

Jyotishmati oil CO2 in 200 mg lower dose ranges from 32-38%,

*Bacopa monnieri* extract CO2 in ranges 3-8%,

The presence of Ginger oil (T) CO2 varies from 0.5-1.5% in lower dose,

The Flax seed oil CO2 used in lower dose is 50-60%,

Rosemary extract CO2 is used in the range of 2-6% in lower dose,

Similarly vitamin E is used in 0.3% to 0.60% in lower dose.

In a preferred embodiment, 'a high dose' formulation 300 mg twice a day as described herein above comprises Jyotishmati oil CO2 in 35%; *Bacopa monnieri* extract CO2 in 5%; Ginger oil (T) CO2 in 1%; Flax seed oil CO2 in 54.6%; Rosemary extract CO2 in 4% and vitamin E in 0.4%. Sesame oil is not used in the higher dose.

In another preferred embodiment, 'a lower dose' formulation 300 mg twice a day as described herein above comprises Jyotishmati oil CO2 in 23.33%; *Bacopa monnieri* extract CO2 in 3.33%; Ginger oil (T) CO2 in 0.67%; Flax seed oil CO2 in 36.4%; Rosemary extract CO2 in 2.66%; vitamin E in 0.27% and Sesame oil in 33.33%.

Alternatively 'a lower dose' formulation 200 mg twice a day without sesame oil as described herein above comprises Jyotishmati oil CO2 in 35%; *Bacopa monnieri* extract CO2 in 5%; Ginger oil (T) CO2 in 1%; Flax seed oil CO2 in 54.6%; Rosemary extract CO2 in 4.00%; vitamin E in 0.40%

In accordance with the above, in 300 mg of capsule, the above herbal extracts in higher and lower doses will be present in the following proportions by wt. This can be used in any dosage form such as solid, liquid and powder form.

| Ingredients | Proportions by Wt | |
|---|---|---|
| | Higher Dose | Lower Dose |
| Jyotishmati Oil $CO_2$ | 105 mg | 70 mg |
| *Bacopa monnieri* Ext. $CO_2$ | 15 mg | 10 mg |
| Ginger Extract $CO_2$ | 3 mg | 2 mg |
| Flax Seed oil $CO_2$ | 163.8 mg | 109.2 mg |
| Rosemary Ext $CO_2$ | 12 mg | 8 mg |
| Vitamin E | 1.2 mg | 0.8 mg |
| Sesame oil | — | 100 mg |

Alternatively 200 mg dosage twice a day without sesame oil:

| Ingredients | Proportions by Wt Lower Dose |
|---|---|
| Jyotishmati Oil $CO_2$ | 70 mg |
| *Bacopa monnieri* Ext. $CO_2$ | 10 mg |
| Ginger Extract $CO_2$ | 2 mg |
| Flax Seed oil $CO_2$ | 109.2 mg |
| Rosemary Ext $CO_2$ | 8.0 mg |
| Vitamin E | 0.8 mg |

In another preferred embodiment, the invention provides the composition in the form of a dietary supplement or herbal medicine in conventional forms of Soft Gel Capsules, Hard Gel Capsules, Liquid Capsules, with or without carrier, dietary powders, drinks, substantially homogeneous mixtures i.e., active ingredients are distributed evenly.

In another preferred embodiment, the present invention provides method of treating using the inventive composition for lowering the symptoms of ADD/ADHD. The compositions of the present invention can be administered in a dosage range of 50 mg to 1000 mg per dose in any of the above mentioned dosage forms. The recommended dose of administration is twice a day.

In yet another embodiment, the present invention provides a method for treating symptoms associated with attention Deficit Disorder (ADD) and Attention Deficit/Hyperactivity Disorder (ADHD), which method comprises administering an effective amount of the 'composition of invention' to the subject suffering symptoms associated with attention Deficit Disorder (ADD) and Attention Deficit/Hyperactivity Disorder (ADHD) for a period of up to 3 to 12 months. The subject mentioned herein is human.

The mode of administration may be 100 mg capsule twice a day or 200 mg capsule twice a day or 300 mg capsule twice a day depending upon the severity of the symptoms of ADHD/ADD. The capsule comprising effective amount required to an individual in need of reducing the symptoms. One more possible mode is administering 100 mg capsule in multiples of 2 or 3 at a time if capsules of 200 mg and 300 mg are not available.

The 'effective amount' as described above means and includes the amount required to treat/alleviate the severity of symptoms associated with this ailments as decided by the persons of ordinary skill in the art.

In one preferred embodiment, the above composition is administered in soft Gelatin Capsules without any use of carrier.

The oral administration may be accomplished by ingesting the composition preferably in soft gel form with a glass of water. The other dosage forms like hard gelatin capsules, powders, liquid capsules, Vegiterian capsules and as additives to food are also equally good modes of administration, at the same recommended dosage two times a day.

The compositions of the invention is also useful effectively in treating the other ailments such as associated disorders with ADHD, Learning disabilities, Tourette Syndrome, Oppositional defiant disorder, Conduct disorder, Bipolar disorder, Dymensia, Parkinson, Alzheimers and Hypertensive Disorder/High Blood Pressure, loss of memory, Austin, OCI PDD-NOS, RETTS, Aspergers, epilepsy, Dyspraxia, Dyslexia, Cerebellar, Ataxia, Down Syndrome, Schizophrenia and other neurodevelopmental disorders that result in leaning and behavioral issues also for improving memory and cognitive skills.

Safety Data:

The composition is absolutely safe for use and has no side effects at the given dosage levels. This can be evident from the sub acute toxicity data presented below: The objective of the study was to determine the long term 90 days continuous exposure, oral toxicity of the composition following OECD guidelines protocol.

Group I: In the control group, all the animals appeared normal and showed no mortality upto the end of the study.

Group II was given a human dose of 200 mg/kg, all the animals appeared normal and showed no mortality upto the end of the study. There was no irritation to GIT after the administration of the drug.

Group II was given human dose of 2000 mg/kg, all the animals appeared normal and showed no mortality upto the end of the study. The dosage was administered for a continuous period of 90 days.

Body weight: There was no statistically significant decrease in the body weight gain in all the study groups when compared with the control group animals.

Food consumption: There was no significant difference observed in the amount of the food compared to the control group.

Haematological data: There was no significant difference observed in the parameters like RBC, WBC total and differential, Hb, PVC and prothrombin time in all the test groups compared with control group.

Further, there was no difference observed in blood chemistry as well as in the organ weights. Urine analysis was normal and no mortality observed. No abnormal findings were observed in Histopathological findings for heart, brain, testis/ovaries. The drug related changes were not seen in any of the test groups compared to control group.

Safety Data on Human Subjects:

From the Clinical Trial Report for 360 Days of Administering the Drug on 47 Patients. Following is the Outcome Safety Evaluation:

For safety evaluation medical history and physical examination were performed at every visit. Additionally, following laboratory investigations were performed at baseline and then at day 90, 180, 270 and 360.

Clinical Laboratory Tests:

1. Complete Blood Count (CBC):
   Hemoglobin, red blood cells (RBC), White blood cell (WBC) and ESR.
2. Blood Chemistry:
   Blood sugar, Bilirubin (Direct & Indirect), alkaline phosphates, SGOT, SGPT, creatinine, uric acid, total protein, albumin and globulin
3. Urine Analysis:
   Colour, specific gravity, pH, protein, glucose, ketones, bilirubin)
4. ECG Further, there was no difference observed in blood chemistry as well as in the organ weights. Urine analysis was normal and no mortality observed. No abnormal findings were observed in Histopathological findings for heart, brain, testis/ovaries. The drug related changes were not seen in any of the test groups compared to control group.

Therefore, it can be concluded that the herbal compositions of the present invention is safe for long term use based on the sub acute toxicity findings as well as human data as described above, as per the OECD guidelines.

Pilot Trials:

Pilot trials have been carried out for dose determination and efficacy of the formulation on the behavioral disorders in adolescent. The results of the pilot study are discussed below in detail.

The trial has been carried out as open labeled study

Number of subjects-8 students of $9^{th}$ Std. diagnosed as behavior disorder cases.

Criteria of Selection of Students

1. DSM IV criteria (diagnostic and statistics manual)
2. Primary physical and mental checkup
3. SPM subjective performance matrices to assess' general intellect.

Criteria Assessment

| 1. DSM IV criteria- | |
| --- | --- |
| Score | Interpretation |
| Above 42 | Hyper |
| 36-42 | High |
| 29-35 | Moderate |
| 22-28 | Moderate |
| 15-21 | moderate |
| 8-14 | Mild |
| 0-7 | Negligible |

| 2 SPM Criteria | |
| --- | --- |
| Percentile Rank | Interpretation |
| Above 95 | Superior |
| 90-94 | High |
| 75-89 | Above average |
| 60-74 | Average+ |
| 40-59 | average |
| 25-39 | Average− |
| 10 to 24 | Below average |
| Below 9 | Poor |

Methodology:

Students of the $9^{th}$ standard having behavior disorders were initially screened on the basis of specially designed questionnaire, which was filled up by respective class teachers. Students of behavior disorders were diagnosed on the basis of criteria of DSM IV. The subjects were subjected to physical and mental check ups to exclude association of any other illness.

Assessment of intellectual status (IQ) was done on the basis of score of PR obtained by standard psychometric test i.e. (SPM) with the help of clinical psychologist. Dose of administration is 125 mg capsule (containing 100 mg of composition described in this invention with weight of gelatin cover 25 mg making a gross weight of capsule 125 mg) administered along with milk. The progress in behavior, mental and intellectual status was recorded every fortnightly. Incidence of any adverse reaction like vomiting, nausea, headache, gastric upset were also noted and were withdrawn from the study accordingly. At the end of the trial (after 90 days) improvement and effect of the formulation was assessed on the basis of the score obtained by SPM and DSM IV.

Observations and results are given below which shows the scores before and after treatment as per DSM IV criteria in Table 1.

TABLE I

| | B.T (Before Treatment) | | A.T (After treatment) | |
| --- | --- | --- | --- | --- |
| Sr. No | Score | Remark | Score | Remark |
| 1. | 10 | Mild | 2 | Negligible |
| 2 | 16 | Moderate | 9 | Mild |
| 3 | 18 | Moderate | 9 | Mild |
| 4. | 23 | Moderate | 9 | Mild |
| 5 | 29 | Moderate | 11 | Mild |
| 6 | 20 | Moderate | 15 | Moderate |
| 7 | 25 | Moderate | 15 | Moderate |
| 8 | 10 | Mild | 2 | Negligible |

Table II given below shows the effect of the formulation as per DSM IV criteria

TABLE II

| No | B.T | A.T | Difference = X |
|---|---|---|---|
| 1 | 10 | 2 | 8 |
| 2 | 16 | 9 | 7 |
| 3 | 18 | 9 | 9 |
| 4 | 23 | 9 | 14 |
| 5 | 29 | 11 | 18 |
| 6 | 20 | 10 | 10 |
| 7 | 25 | 15 | 10 |
| 8 | 10 | 2 | 8 |
| | | Total | 84 |

Mean difference: =10.5
SD=$3.70^2$
SE=1.309
t7=8.019
At 7 degree of freedom 15%, Significant limit of t is 2.37. Therefore ('t7'=8.019, p<0.001 reduction in symptoms of ADHD statistically highly significant.

Table III given below shows the intellectual status before and after treatment as per SPM.

TABLE III

| Sr. No | Raw Score | PR | interpretation | Raw score | PR | Interpretation |
|---|---|---|---|---|---|---|
| 1 | 45 | 68 | Average+ | 53 | 90 | high |
| 2 | 37 | 23 | Below average | 39 | 25 | Average– |
| 3 | 43 | 50 | Average | 50 | 86 | Above average |
| 4 | 36 | 17 | Below average | 38 | 22 | Below average |
| 5 | 34 | 24 | Below average | 38 | 41 | Average |
| 6 | 48 | 75 | Above average | 53 | 90 | High |
| 7 | 42 | 35 | Average– | 43 | 35 | Average |
| 8 | 44 | 68 | Average+ | 45 | 68 | Average+ |

Table IV shows intellectual status before and after treatment as per SPM.

TABLE IV

| No | BT(A) | BT(B) | Difference X = (B − A) | Mean X − X̄− X̄− = 12.1 | $(X − \bar{X}-)^2$ |
|---|---|---|---|---|---|
| 1 | 68 | 90 | 22 | 10.9 | 118.81 |
| 2 | 23 | 25 | 2 | −10.1 | 102.01 |
| 3 | 50 | 86 | 36 | 23.9 | 571.21 |
| 4 | 17 | 22 | 5 | 7.1 | 50.41 |
| 5 | 24 | 41 | 17 | 5.1 | 26.01 |
| 6 | 75 | 90 | 15 | 3.1 | 9.61 |
| 7. | 35 | 35 | 0 | 12.1 | 146.41 |
| 8 | 68 | 68 | 0 | 12.1 | 146.41 |
| | | total | 97 | | 1170.88 |

X̄=12
S.D=12.93
S.E=4.57
t7=2.65
At 7 degrees of freedom, 5% significant limit of t is 2.37. Hence the mean improvement in general intelligence is significant at 5% level. (t=2.65, P<0.05)

Results in Table I and II indicates that there was marked reduction in the post treatment scores of all the 8 students. The analysis of the results on the basis of paired test revealed that the formulation significantly reduced the scores of symptoms of behavior disorders as stated in DSM IV.

Results of Table III and IV:

After treatment, the scores of percentile rank (PR) as compared to initial score as per SPM of 8 students suggested some improvement however; raw score of each student is markedly improved.

Statistical analysis as per paired test showed significant improvement (P<0.05) in PR of 8 students after the treatment for 3 months suffering from behavior disorder. One student complained of nausea and was withdrawn from the trial after 50 days.

From the above trials, it has been concluded that the herbal formulation of the present invention has positive effect on the subject who is suffering with Attention deficit disorder as the symptoms are relieved significantly. It was also confirmed that the administration of inventive composition for 3 months, significantly improves the cognitive skills of the students suffering from behavior disorders. Thus the inventive formulation has notropic as well as psychotropic effect on the patients suffering from ADD/ADHD.

The following examples, which include preferred embodiments, will serve to illustrate the practice of this invention, it being understood that the particulars shown are by way of example and for purpose of illustrative discussion of preferred embodiments of the invention.

The current herbal formulation not only treats symptoms of ADHD but also cures the disease with no side effects. The current invention provides a synergistic herbal composition for the treatment of ADHD comprising extracts and oils of $CO_2$ of following herbs in the portion as indicated with below ingredients.

EXAMPLES

Example 1

In 100 mg of capsule the said herbal extracts are used in the following proportions by weight (wt).

| Ingredients | Proportions by Wt. |
|---|---|
| Jyotishmati Oil CO2 | 35 mg |
| *Bacopa monnieri* Ext. CO2 | 5 mg |
| Ginger Oil (T) CO2 | 1 mg |
| Flax Seed oil CO2 | 54.6 mg |
| Rosemary Ext CO2 | 4 mg |
| Vitamin E | 0.4 mg |

For lower dose: 2 capsules of 100 mg two times a day is used.

For higher dose: 3 capsules of 100 mg two times a day is used.

Example 2

Alternatively, lower dose can also be administered as described below in a 300 mg capsule.

| 1) Lower Dose: (300 mg) | Proportion by weight | |
|---|---|---|
| Jyotishmati Oil CO2 | 70 mg | 20-26% |
| *Bacopa monnieri* ext. $CO_2$ | 10 mg | 2-6% |

-continued

| 1) Lower Dose: (300 mg) | Proportion by weight | |
|---|---|---|
| Ginger Oil (T) $CO_2$ | 2 mg | 0.5-0.8% |
| Flax Seed Oil $CO_2$ | 109.2 mg | 32-40% |
| Rosemary Ext. $CO_2$ | 8 mg | 2-5% |
| Vitamin E | 0.8 mg | 0.17-0.30% |
| Sesame oil | 100 mg | 30-35% |
| Total | 300 mg | |

Example 3

Alternatively higher dose can also be administered as described below in a 300 mg capsule.

| | Proportion by weight | |
|---|---|---|
| II) Higher Dose (300 mg): - | | |
| Jyotishmati Oil $CO_2$ | 105 mg | 32-38% |
| Bacopa monnieri Ext. $CO_2$ | 15 mg | 4-7% |
| Ginger Oil (T) $CO_2$ | 3 mg | 0.5-1.5% |
| II) Higher Dose (300 mg): - | | |
| Flax Seed oil $CO_2$ | 163.8 mg | 51-58% |
| Rosemary Ext. $CO_2$ | 12 mg | 3.0-6.0% |
| Vitamin E | 1.2 mg | 0.3-0.6% |
| | 300 mg | |

Example 4

The said herbs are used in the following proportions by wt %

| Ingredients | Higher Dose (300 mg bid) | Lower dose (200 mg bid) | Alternative Lower dose (300 mg bid) |
|---|---|---|---|
| Jyotishmati Oil $CO_2$ | 35% | 35.00% | 23.33% |
| Bacopa Monnien Ext. $CO_2$ | 5% | 5.00% | 3.33% |
| Ginger Oil (T) $CO_2$ | 1% | 1.00% | 0.67% |
| Flax Seed oil $CO_2$ | 54.6% | 54.6% | 36.4% |
| Rosemary Ext. $CO_2$ | 4% | 4.00% | 2.66% |
| Vitamin E | 0.4% | 0.40% | 0.27% |
| Sesame oil | Not Added | Not added | 33.33% |

Example 5

In 300 mg of capsule the said herbal extracts are used in the following proportions by wt.

| | Proportions by Wt. | | |
|---|---|---|---|
| Ingredients | Higher Dose | Lower Dose | Alternative Lower Dose |
| Jyotishmati Oil $CO_2$ | 105 | 70 mg | 70 mg |
| Bacopa monnieri Ext. $CO_2$ | 15 | 10 mg | 1.0 mg |
| Ginger Oil (T) $CO_2$ | 3 | 2 mg | 2 mg |
| Flax Seed oil $CO_2$ | 163.8 | 109.2 mg | 109.2 mg |
| Rosemary Ext $CO_2$ | 12 | 8 mg | 8 mg |
| Vitamin E | 1.2 | 0.8 mg | 0.8 mg |
| Sesame oil | — | — | 100 mg |

Example 6

The parts of the herbs used in the composition of invention are as below:

| Ingredients | Parts of the herb |
|---|---|
| Jyotishmati Oil $CO_2$ | Dried Seeds |
| Bacopa monnieri Ext. $CO_2$ | Whole Plant |
| Ginger Oil (T) $CO_2$ | Dried rhizomes |
| Flax Seed oil $CO_2$ | Dried Seeds |
| Rosemary Ext $CO_2$ | Aerial parts |
| Sesame Oil | Dried Seeds |

The active ingredients of $CO_2$ extracts and oils of *Celastrus paniculatus*, *Linum usitatissimum*, *Bacopa monnieri*, *Zingiber officinalis* and Rosemary is obtained by the following process steps:
1. Shade drying the fresh and dust free herbs parts required for extraction;
2. Grinding of these plant parts to make fine powder after drying;
3. Transferring these fine powders into extraction chamber;
4. Passing the high pressure $CO_2$ through it for a predetermined time and at predetermined temperature; and
5. Removing the $CO_2$ extracts or oils through separator.

Example 7

Synopsis of Clinical Evaluation of the Composition of Invention

A Study of Safety and Efficacy of Capsule C on ADD/ADHD (Attention Deficit Hyperactivity Disorder) in Adolescents was Carried Out with Following Objectives:
Primary End Point:
1. Reduction in ADHD Score.
2. Clinically meaningful reduction in ADHD symptoms.
Secondary Endpoint:
3. Improvement in scholastic performance of student.
4. Improvement in Intelligent Quotient (IQ) of student.
5. Overall improvement in mental status
Safety Evaluation for the Composition for Long Term Intervention:

School children were predominantly screened on the basis of questionnaires and the Diagnostic and Statistical Manual of Mental Disorders (4th ed.) criteria (DSM-IV) for hyperactivity after taking written informed consent from school principal of one of the leading High School, in Pune as well as their parents. Those children who were found to be hyperactive as per parents and teachers questionnaires, were informed about the study and informed consent were taken for enrollment of their child in the study. Further these children were evaluated for inclusion exclusion criteria and also undergone lab and ECG investigations. Those who found to be eligible were enrolled in the study. Subjects were randomized to one of the two treatment groups.

Per Protocol Analysis:

First Phase Study:

The subjects were enrolled in a double blind and randomized fashion. The subjects were randomized to one of the two treatment groups (Group A and B). Those randomized to Group A received placebo 2 caps 100 mg twice a day for 3 months (49 subjects). Subjects randomized to Group B received capsule C 2 caps 100 mg twice a day for 3 months (48 subjects). All the subjects underwent medical and physical examination and evaluation for ADHD Dupal's score every 15 days. Duration of $1_{st}$ Phase was 3 months. Placebo capsules contain 100 mg sesame oil. Capsule C contains 100 mg of formulation as described in the current invention. The Comparison of efficacy between placebo and Capsule C is discussed in table V.

TABLE V

Comparison of efficacy between placebo and Capsule C

| Time point | Dupaul's ADHD score | | Significance | |
| | Group A (Placebo) (n = 39) | Group B (Capsule C) (n = 32) | Level (Group A Vs Group B) | Significance |
| --- | --- | --- | --- | --- |
| Baseline | 19.84 ± 5.28 | 18.88 ± 3.81 | 0.39 | NS |
| 90 days | 9.86 ± 5.45 | 6.96 ± 3.54 | 0.01 | HS |

** Unpaired 't' test is applied, p value is significant if p < 0.05.
NS—Not Significant
HS—Highly significant From the above, in-group A, mean Dupaul's ADHD scale scores were 19.84 and 9.86 at baseline and at 3 months respectively. Corresponding findings in-group B were 18.88 and 6.96 respectively. ADHD score reduced from baseline to 90 days in both the groups. There is no statistically significant difference between the ADHD score of group A and Group B at baseline but the difference is significant at the end of 90 days. This clearly shows that the capsule C is highly effective in reducing the symptoms of ADHD.

Evaluation as Per DSM IV Criteria:

As per DSM IV criteria, in combined type of ADHD, 54.05% subjects showed improvement at 3 months in Group A (placebo), while 73.52% subjects showed improvement in Group B (capsule C). In predominantly Inattentive type, 63.63% subjects showed improvement at 3 months in Group A (placebo), while 85.71% subjects showed improvement in Group B (capsule C) and in predominantly Hyperactive-Impulsive type, 87.5% subjects showed improvement at 3 months in Group A (placebo), while 90.90% subjects shows improvement in Group B (capsule C). This clearly shows efficacy of the composition for improving the symptoms of ADD/ADHD. The details are given in table VI.

TABLE VI

Efficacy measurement at baseline and at 90 day (PPP analysis).

| | | Number & Percentage | |
| Type of ADHD | Study Groups | At baseline DSM IV score (Score ≧ 6) | At 90 day DSM IV score (Score < 6) |
| --- | --- | --- | --- |
| Combined type | Placebo | 37 (100%) | 20 (54.05%) |
| | Capsule | 34 (100%) | 25 (73.52%) |
| Predominantly Inattentive Type | Placebo | 33 (100%) | 21 (63.63%) |
| | Capsule | 28 (100%) | 24 (85.71%) |
| Predominantly Hyperactive-Impulsive Type | Placebo | 16 (100%) | 14 (87.5%) |
| | Capsule | 11 (100%) | 10 (90.90%) |

Second Phase Study:

Evaluation of the Composition for Long Term Safety and Efficacy (91st Day to 360th Day):

In second phase, the subjects were enrolled in an open label and non-randomized fashion. Responders, who exhibited at least 30% reduction in their symptoms, were calculated on the basis of Dupaul's scale and DSM IV in both the groups. The responders from the study group were continued for further study and higher dose of the study drug was given to them. The non-responders, who received Capsule C in first phase, were excluded from the study.

In this phase of the study, the subjects were enrolled in two groups. In Group A, all the subjects who responded to Capsule C and 50% of subjects who responded to placebo in first phase were enrolled. In Group B, remaining 50% of subjects who received placebo in first phase were enrolled.

Group A subjects received 3 capsule of Capsules C (higher dose) twice a day while Group B subjects received 2 capsule of Capsules C (lower dose) twice a day. The dose pattern was continued till the end of the study. Subjects were followed through 90 to 360 days. All the subjects underwent medical and physical examination every 15 days. DSM IV criteria and assessment of ADHD on Dupaul's ADHD scale were also performed every 15 days. Mental examination was carried out monthly and intelligent quotient at baseline and day 90, 180, 270 and 360.

Clinical laboratory tests were performed at baseline and at day 90, 180, 270 and 360. Parents were inquired for development of adverse and serious adverse event at each visit.

Efficacy in Second Phase:

The objective of this phase was to establish the long term efficacy and safety of the high as well as low dose of capsule C.

Second Phase (High Dose Vs Low Dose):

Mean Dupaul's ADHD scale scores of subjects receiving higher dose are 6.3, 7.8, 6.4 and 8.0 at 90 days, 180 days, 270 days and 360 days respectively. Corresponding findings in subjects receiving lower dose were 10.2, 9.7, 7.9 and 7.9 at 90 days, 180 days, 270 days and 360 days respectively. Significant difference was seen between the ADHD score of group A and Group B at 90 days. No significance difference was seen at 180 days, 270 days and 360 days. The details are given in table VII.

TABLE VII

Comparison of efficacy between two doses of Capsule C.

| Time point | Dupaul's ADHD score Higher dose | Dupaul's ADHD score Lower dose | Significance Level | Significance |
|---|---|---|---|---|
| 90 days | 6.3 ± 3.3 | 10.2 ± 6.3 | 0.01 | HS |
| 180 days | 7.8 ± 5.3 | 9.7 ± 7.4 | 0.28 | NS |
| 270 days | 6.4 ± 4.9 | 7.9 ± 6.5 | 0.37 | NS |
| 360 days | 8.0 ± 6.8 | 7.9 ± 7.6 | 0.96 | NS |

** Unpaired 't' test is applied, p value is significant if p < 0.05.

Mental Examination (IQ Scores of Student):

The mean mental examination score improved from baseline to 360 days in both the groups. Following table shows the statistical analysis of IQ scores for both the groups.

IQ Analysis:

|  | 0 day IQ | $360^{th}$ IQ |
|---|---|---|
| n | 85 | 47 |
| Mean | 87.13 | 90.11 |
| SD | 5.59 | 9.45 |
| Paired t test | | |
| Day 0 Vs 360 | | 0.024* |

The 1 year completers shows statistically significant difference in the IQ scores at the end of the phase III ($360^{th}$ day) than that of baseline ($0^{th}$ day) by parametric as well as non-parametric tests.

Moreover, the mean mental examination score improved from 0 days to 360 days in both the groups but the difference between mean changes in score is not statistically significant. This indicates that both the higher dose as well as lower dose is improving the IQ scores on Weschler scale Scholastic performance was considered as one of the criteria in assessing the results of the study treatments. Moreover, sitting at a place and studying is generally difficult for an ADD/ADHD child. Hence duration for which a student sits and study was noted. Irrespective of the results of the exams, an increase in the study time would point towards the efficacy of the drug. An increase in attentiveness and decrease in the hyperactivity leads to increased study time.

All the students were evaluated for progress in various subjects (Marathi, Hindi, English, Mathematics, science, social science) in mid semester and final examination conducted by the schools to see the improvement. There was a marked improvement in the study time as well as scholastic performance when the scores of first and second semester were examined statistically.

Conclusion:

From the above it is evident that 'Capsule C' significantly improves the symptoms of ADHD as compared to placebo in children and adolescents of 8-16 years of age. The treatment is also effective in improving the core symptoms of ADHD, namely inattention, hyperactivity, and impulsivity, both at school and at home. Lower dose of the capsule C is as good as high dose and effective and safe when used for long period of time.

Example: 8

Effect of Capsule C on the FA Profile Post Treatment

In this trial, 23 patients were administered higher dose of capsule c (one 300 mg capsule two times a day) to study the effect of capsule C on Fatty acid profile in the patients blood. Blood samples were collected from all the subjects before administering the capsule on 0th day and then a blood sample was obtained on 90th day. Samples were analyzed at Dept. of Biotechnology, Sinhgad College of Engineering, Pune.

Method of Analysis:

Fatty Acid Analysis:

RBCs samples were analyzed. Isolation of fatty acids and methyl esterification of fatty acids was done by the following method:
1. Extracting lipids using 2:1 chloroform/methanol.
2. Methyl esterification with Methanolic HCl (0.6N HCl/methanol) at 80° C. for 2 hrs.
3. Separating the esters and quantifying on GC by capillary column (BPX 70)

Thiobarbituric Acid Reactive Assay (TBAR):
1. Treating Plasma with 10% TCA (Trichloro aceticacid) and then with 0.6% TBA (Thiobarbituaric Acid).
2. Heat treating it for 10 mins at 90° C.
3. Centrifugating at 3000×g for 10 mins and then reading optical density at 530 nm against water blank.

Statistical Analysis:

The statistical analysis of the data was done using software (Software for Statistical Programme for Social Sciences).

TABLE VIII

Percentage distribution of FAMEs in ADHD patients:

|  | Period | Area percentage distribution of fatty acids SFA | MUFA | LA | ALA | AA | EPA | DHA | TBAR mM |
|---|---|---|---|---|---|---|---|---|---|
| Mean | Pre | 86.98 | 5.9 | 4.41 | 1.11 | 0.64 | 0.37 | 0.76 | 0.061 |
|  | Post | 82.58 | 8.6 | 6.57 | 1.23 | 0.42 | 0.47 | 2.04 | 0.039 |
| P value |  | $0.00^1$ | $0.02^1$ | $0.00^1$ | 0.57 | $0.04^2$ | 0.44 | $0.01^1$ | $0.02^1$ |

SFAs, saturated fatty acids; MUFAs, monounsaturated fatty acids; LA, linoleic acid; ALA, á-linolenic acid; AA, arachidonic acid; EPA, eicosapentanioc acid; DHA, decosahexanoic acid.
[1]P < 0.05 (T test value) significant,
[2]P > 0.05 & < 0.08 (T test value) near significance.

Conclusion:

The experimental analysis of the given samples showed that there was highly significant increase in levels of MUFA, LA, DHA levels post supplementation. The percentage distribution of SFA and AA significantly decreased post treatment. The TBAR analysis showed that there was a significant decrease in oxidative stress post treatment.

INDUSTRIAL APPLICABILITY

Capsule C was well tolerated in this patient population. No adverse events were reported in clinical study. The occurrence of abnormal laboratory values was low and similar in both placebo and capsule C groups. No apparent trends were seen and most were considered to be clinically insignificant. No clinically significant changes in mean ECG parameters were observed over the duration of the study; in all cases where abnormalities occurred, findings were deemed harmless, clinically insignificant, or normal by pediatric cardiologists. In regard to vital signs, no significant changes were seen between treatment groups and no significant changes occurred over time. No discontinuation is reported for safety reason. This is one of the significant finding, since atomoxetine and other standard treatment modalities (methylphenidate) are responsible for more than 10% discontinuations for adverse events.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A herbal composition comprising: Jyotishmati oil (*Celastrus paniculata* seed oil) in an amount of about 5 to 50% of the total formulation; Flax seed oil (*Linum usitatissium* seeds) in an amount of about 30 to 65%; *Bacopa monnieri* extract in an amount of from greater than 0% to about 10%; *Rosmarinus officinalis* extract from greater than 0% to about 10%; Ginger (*Zingiber officinalis*) extract in an amount of from greater than 0% to about 4%; and natural Vitamin E (α Tocopherols) in an amount of from greater than 0% to about 2%%, said composition being useful in the treatment of symptoms associated with Attention Deficit disorder (ADD) or Attention deficit/hyperactivity disorder (ADHD).

2. The herbal composition as claimed in claim 1, wherein said composition optionally comprises sesame oil.

3. The herbal composition as claimed in claim 1, wherein said composition in comprises:
from 32% to 38% by weight of Jvotishmati oil obtained through extraction with supercritical carbon dioxide;
from 4% to 7% by weight of *Bacopa monnieri* extract obtained through extraction with supercritical carbon dioxide;
from 0.5% to 1.5% by weight of Ginger extract obtained through extraction with supercritical carbon dioxide;
from 51% to 58% by weight of Flax seed oil obtained through extraction with supercritical carbon dioxide;
from 3% to 6% by weight of Rosemary extract obtained through extraction with supercritical carbon dioxide; and
from 0.3% to 0.6% by weight of Vitamin E.

4. The herbal composition as claimed in claim 3, wherein said composition comprises:
35% by weight of Jyotishmati oil obtained through extraction with supercritical carbon dioxide;
5% by weight of *Bacopa monnieri* extract obtained through extraction with supercritical carbon dioxide;
1% by weight of Ginger oil obtained through extraction with supercritical carbon dioxide;
54.6% by weight of Flax seed oil obtained through extraction with supercritical carbon dioxide;
4% by weight of Rosemary extract obtained through extraction with supercritical carbon dioxide; and
0.4% by weight of Vitamin E.

5. The herbal composition as claimed in claim 1, said composition further comprising Sesame oil;
wherein said herbal composition comprises from 20% to 26% by weight of Jyotishmati oil obtained through extraction with supercritical carbon dioxide;
from 2% to 6% by weight of *Bacopa monnieri* extract obtained through extraction with supercritical carbon dioxide;
from 0.5% to 0.8% by weight of Ginger oil obtained through extraction with supercritical carbon dioxide;
from 32% to 40% by weight of Flax seed oil obtained through extraction with supercritical carbon dioxide;
from 2% to 5% by weight of Rosemary extract obtained through extraction with supercritical carbon dioxide;
from 30% to 35% by weight of Sesame oil and
from 0.17% to 0.30% by weight of Vitamin E.

6. The herbal composition as claimed in claim 5, wherein said composition comprises:
23.33% by weight of Jvotishmati oil obtained through extraction with supercritical carbon dioxide;
3.33% by weight of *Bacopa monnieri* extract obtained through extraction with supercritical carbon dioxide;
0.67% by weight of Ginger oil obtained through extraction with supercritical carbon dioxide;
36.4% by weight of Flax seed oil obtained through extraction with supercritical carbon dioxide;
2.66% by weight of Rosemary extract obtained through extraction with supercritical carbon dioxide;
33.33% by weight of Sesame oil and
0.27% by weight of Vitamin E.

7. The herbal composition as claimed in claim 1, wherein said composition optionally comprises a pharmaceutical excipient.

8. The herbal composition as claimed in claim 7, wherein said pharmaceutical excipient is selected from the group consisting of binders, diluents, lubricants, disintegrants, pharmaceutical oils and bases, and mixtures thereof.

9. The herbal composition as claimed in claim 1, wherein:
said extract of Jyotishmati oil is an Jyotishmati seeds;
said extract of Ginger is an extract of ginger rhizome; and
said extract of Rosemary is an extract of aerial parts of a rosemary plant.

10. A method of treating a patient exhibiting symptoms associated with attention Deficit Disorder (ADD) and Attention Deficit/Hyperactivity Disorder (ADHD) comprising administering a composition according to claim 1 to said patient.

11. A method for treating symptoms associated with Attention Deficit disorder (ADD) and Attention deficit/hyperactivity disorder (ADHD), which method comprises administering an effective amount of the composition of claim 1 to the subject suffering symptoms associated with attention Deficit Disorder (ADD) and Attention Deficit/Hyperactivity Disorder (ADHD) for a period of up to 3 to 12 months.

12. The method as claimed in claim 11, wherein said subject is human.

13. A method of treating a patient exhibiting symptoms associated with attention Deficit Disorder (ADD) and Attention Deficit/Hyperactivity Disorder (ADHD) comprising administering a composition according to claim 3 to said patient.

14. A method of treating a patient exhibiting symptoms associated with attention Deficit Disorder (ADD) and Attention Deficit/Hyperactivity Disorder (ADHD) comprising administering a composition according to claim 5 to said patient.

* * * * *